US006531277B2

(12) United States Patent
Timms

(10) Patent No.: US 6,531,277 B2
(45) Date of Patent: *Mar. 11, 2003

(54) ENDOMETRIOSIS-SPECIFIC SECRETORY PROTEIN

(75) Inventor: Kathy L. Timms, Columbia, MO (US)

(73) Assignee: The Curators of the University of Missouri, Columbia, MO (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/044,604

(22) Filed: Mar. 19, 1998

(65) Prior Publication Data

US 2002/0009718 A1 Jan. 24, 2002

Related U.S. Application Data

(63) Continuation-in-part of application No. 08/328,451, filed on Oct. 25, 1994, now abandoned.

(51) Int. Cl.[7] .......................... C07H 21/04; C12Q 1/68; G01N 33/567

(52) U.S. Cl. .......................... 435/6; 435/7.21; 435/975; 436/503; 436/87; 536/23.5

(58) Field of Search .......................... 435/6, 806, 7.21, 435/975; 436/65, 87, 814, 906, 503; 536/23.5; 935/4

(56) References Cited

U.S. PATENT DOCUMENTS

| | | | |
|---|---|---|---|
| 3,791,932 | A | 2/1974 | Schuurs et al. |
| 3,839,153 | A | 10/1974 | Schuurs et al. |
| 3,850,578 | A | 11/1974 | McConnell |
| 3,850,752 | A | 11/1974 | Schuurs et al. |
| 3,853,987 | A | 12/1974 | Dreyer |
| 3,867,517 | A | 2/1975 | Ling |
| 3,879,262 | A | 4/1975 | Schuurs et al. |
| 3,901,654 | A | 8/1975 | Gross |
| 3,935,074 | A | 1/1976 | Rubenstein et al. |
| 3,984,533 | A | 10/1976 | Uzgiris |
| 3,996,345 | A | 12/1976 | Ullman et al. |
| 4,034,074 | A | 7/1977 | Miles |
| 4,098,876 | A | 7/1978 | Piasio et al. |
| 4,879,219 | A | 11/1989 | Wands et al. |
| 5,011,771 | A | 4/1991 | Bellet et al. |
| 5,281,521 | A | 1/1994 | Trojanowski et al. |

FOREIGN PATENT DOCUMENTS

EP WO9008324 7/1990

OTHER PUBLICATIONS

Yang et al., 1983. Identification and characterization of human haptoglobin cDNA. Proc. Natl. Acad. Sci. USA 80: 5875–5879.*

Boe et al., 1994. Determination of haptoglobin expression in IL–6 treated HepG2 cells by ELISA and by RNA hybridization—Evaluation of a quantitative method to measure IL–6. Journal of Immunological Methods 171: 157–167.*

Raugei et al., 1983. Sequence of human haptoglobin cDNA: evidence that the α and β subunits are coded by the same mRNA. Nucleic Acids Research 11: 5811–5819.*

Nothnick et al., 1994. Detection of a unique 32–kd protein in the peritoneal fluid of women with endometriosis. Fertility and Sterility 61: 288–293.*

Dunselman et al., 1988. The acute–phase response in endometriosis of women. J. Reprod. Fert. 83: 803–808.*

Olson et al., Jan. 1997. Specific expression of haptoglobin mRNA in implantation–stage rabbit uterine epithelium. J. Endocrinol. 152: 69–80.*

Bischof and Meisser, 1989. Immunological heterogeneity of pregnancy–associated protein–A (PAPP–A). Effects on the radioimmunoassay of PAPP–A. Br J Obstet Gynaec 96:870–5. [n/a—will mail in].

Bueller and Bersinger, 1989. Antisera to pregnancy–associated plasma protein–A (PAPP–A) recognizes human haptoglobin. Br J Obstet Gynaec 96:867–9. [n/a—will mail in].

Dennis, 1995. A review of the biological significance of carbohydrates on glycoproteins and methods for their analysis. Adv Exp Med Biol 376:1–11. [n/a—will mail in].

Dobryszycka, 1992. Relevance of haptoglobin in clinical medicine. Folia Histochemica et Cytobiologica 30:197–200. [n/a—will mail in].

Johnson et al, 1992. Cerebrospinal fluid protein variations in common to Alzheimer's disease and schizophrenia. Applied and Theoretical Electrophoresis 3:46–53. [n/a—will mail in].

Kawasaki Es. Amplification of RNA. In: PCR protocols: A Guide to Methods and Applications, Innis MA, Gelfand DH, Sninsky JJ, White TJ, eds. Academic Press, 1990, pp21–27.

Myrick, et al., 1990. Identification of haptoglobin alpha–2FF variants in mid–trimester maternal serum as potential markers for Down syndrome. Applied and Theoretical Electrophoresis 1:233–41. [n/a—will mail in].

(List continued on next page.)

*Primary Examiner*—Christopher L. Chin
*Assistant Examiner*—James L. Grun
(74) *Attorney, Agent, or Firm*—Kohn & Associates, PLLC

(57) ABSTRACT

A method and kit of diagnosing endometriosis in a female patient suspected of having endometriosis is disclosed. The method includes obtaining a sample from the patient. The sample is analyzed to detect the presence of ENDO -I glycoprotein or its mRNA in the sample compared to non-endometriosis controls who do not express ENDO-I. The protein is characterized by (i) a molecular weight of 40,000 to 55,000 as determined by two-dimensional SDS-PAGE polyacrylamide gel electrophoresis; (ii) having an isoelectric point of 4.0 to 5.5; and (iii) being synthesized and secreted specifically by stromal cells of endometriotic tissue origin; and (iv) in humans having a cDNA as set forth in SEQ ID No:1. The present invention further discloses a cDNA for human ENDO-I (SEQ ID No:1) and antibody directed against ENDO-I.

5 Claims, 2 Drawing Sheets-

OTHER PUBLICATIONS

Oh et al, 1992. Quantitative differentiation of the haptoglobin–related gene product from haptoglobin in human plasma: a possible test of tumor–associated antigen. Hybridoma 11:1–12. [n/a—will mail in].

Bell SC, "Purification of human secretary pregnancy–associated endometrial . . . " *Hum Reprod* 1:313–18 (1986).

Bolen et al., "Reactive and neoplastic serosal tissue". *Am J Surg Path* 10:34–47 (1986).

Catty and Raykundalia, "ELISA and related enzyme immunoassays". In: Catty D (ed) *Antibodies, A Practical Approach*. IRL Press, Oxford. vol. II pp. 97–154.

Cornillie et al., "Expression of endometrial protein PP14 in pelvic and ovarian endometriotic implants" *Hum Reprod* 6:1141–1415 (1991).

Critchley et al., "Role of the ovary in the synthesis of placental protein–14" *J Clin Endocrinol Metab* 75:97–100 (1992).

Haining et al., Epidermal growth factor in human endometrium . . . *Hum Reprod* 6:1200–5 (1991).

Hillam et al., "Local antibody production against the murine toxin of yersinia pestis in a golf ball–induced granuloma" *Infect Immun* 10:458–463 (1974).

Hsu et al., "Use of avidin–biotin–peroxidase comples (ABC) in immunoperoxidase techniques: a comparison . . . " *J. Histochem Cytochem* 29:577–580 (1981).

Isaacson et al., "Production and secretion of complement component 3 by endometriotic tissue" *J Clin Endocrin Metab* 69:1003–9 (1989).

Joshi et al., "Serum levels of a progestagen–associated endometrial protein during the menstrual cycle and pregnancy" *J Clin Endo Metab* 55:642–648 (1982).

Joshi et al., "Radioimmunoassay for a progestagen–associated protein of the human endometrium" *J. Clin Endo Metab* 52:1185–1192 (1981).

Julkunen et al., "Complete amino acid sequence of human placental protein 14: a progesterone–regulated uterine protein homologus . . . " *Proc. Natl. Acad Science USA* 85:8845–49 (1988).

Knudsen KA, "Proteins transferred to nitrocellulose as immunogens" *Anal Biochem* 147:285–288 (1985).

Kruitwagen et al. "Immunocytochemical marker profile of endometriotic epithelial, endometrial epithelial . . . " *European J Obstet Gynecol Reprod Biol* 41:215–223 (1991).

Lessey et al., "Immunohistochemical analysis of estrogen and progesterone receptors in endometriosis: . . . " *Fertil Steril* 51:409–15 (1989).

Melega et al., "Tissue factors influencing growth and maintenance of endometriosis" *Ann NY Acad Sci.* 622:257–65 (1991).

Osteen et al., "Development of a method to isolate and culture highly purified populations of stromal and epithelial cells . . . " *Fertil Steril* 52:965–72 (1989).

Riittinen, L. "Serous ovarian cyst fludis contain high levels of endometrial placental protein 14" *Tumor Biol* 13:175–9 (1992).

Seppala et al. "Endometrial proteins: A reappraisal" *Hum Reprod* 7:31–8 (1992).

Sharpe et al., "Detection of a progesterone–induced secretory protein synthesized by the uteri . . . " *Fertil Steril* 55:403–10 (1991).

Sharpe et al., "Proliferative and morphogenic changes induced by the coculture of rat uterine and peritoneal cells . . . " *Fertil Steril* 58:1220–9 (1992).

Sharpe et al., "Polypeptides synthesized and released by rat endometriotic tissue differ from those . . . " *Biol Reprod* 48:1334–1340 (1993).

Sharpe et al., "Polypeptides synthesized and released by human endometriosis tissue differ from those of the uterine . . . " *Fertil Steril* 60:839–51 (1993).

Telimaa et al., "Elevated serum levels of endometrial secretory protein PP14 in patients with advanced endometriosis" *Am J Obstet Gynecol* 161:866–71 (1989).

Vernon et al., "Classification of endometriotic implants by morphologic appearance and capacity to synthesize . . . " *Fertil Steril* 801–806 (1986).

Vierikko et al., Steriodial regulation of endometriosis tissue: lack of induction of . . . *Fertil Steril* 43:218–224 (1985).

Weibel ER, "Sterological Methods" In: *Practical Methods for Biological Morphometry*, vol. 1, NY: Acadmic Press, pp. 33–45 (1979).

Kuhajda et al., "Haptoglobin–Related Protein (Hpr) Epitopes In Breast Cancer As A Predictor Of Recurrence Of the Disease" *N Engl J Med* 321:636–641 (1989).

Kuhajda et al., "Expression of Haptoglobin–Related Protein And Its Potential Role As A Tumor Antigen" *Proc. Natl. Acad. Sci. USA* 86:1188–1192 (1989).

Kuhajda et al., "Fatty Acid Synthesis: A Potential Selective Target For Antieoplastic Therapy" *Proc. Natl. Acad. Sci. USA* 91:6379–6383 (1994).

Shurbaji et al., "Expression Of Oncogenic Antigen 519 (OA–519) In Prostate Cancer Is A Potential Prognostic Indicator" *Am J Clin Pathol* 97:686–691 (1992).

Shurbaji et al., "Expression Of Haptoglobin–Related Protein In Primary And Metastatic Breast Cancers" *Am J Clin Pathol* 96:238–242 (1991).

Shurbaji et al, "Expression Of Oncogenic Antigen 519 (OA–519) In Prostate Cancer Is a Potential Prognostic Indicator" *Am J Clin Pathol* 97:686–691 (1992).

* cited by examiner

SEQUENCE LISTING

```
(1) GENERAL INFORMATION:

   (iii) NUMBER OF SEQUENCES: 11


(2) INFORMATION FOR SEQ ID NO:1:

     (i) SEQUENCE CHARACTERISTICS:
          (A) LENGTH: 855 base pairs
          (B) TYPE: nucleic acid
          (C) STRANDEDNESS: single
          (D) TOPOLOGY: linear

    (ii) MOLECULE TYPE: cDNA

   (iii) HYPOTHETICAL: NO

    (iv) ANTI-SENSE: NO

    (vi) ORIGINAL SOURCE:
          (A) ORGANISM: Homo sapiens

    (xi) SEQUENCE DESCRIPTION: SEQ ID NO:1:

TAAGATGGTT TCCCACCATA ATCTCACCAC AGGTGCCACG CTGATCAATG AACAATGGCT     60

GCTGACCACG GCTAAAAATC TCTTCCTGAA CCATTCACAA AATGCAACAG CGAAAGACAT    120

TGCCCCTACT TTAACACTCT ATGTGGGGAA AAAGCACCTT GTAGAGATTG AAAAGGTTGT    180

TCTACACCCC AACTACTCCC AGGTAGATAT TGGGCTCATC AAACTCAAAC AGAAGGTGTC    240
```

-continued

```
TGTTAATGAG AGAGTGATGC CCATCTGCCT ACCTTCAAAG GATTATGCAG AAGTAGGGCG    300

TGTGGGTTAT GTTTCTGGCT GGGGGCGAAA TGCCAATTTT AAATTTACTG ACCATCTGAA    360

GTATGTCATG CTGCCTGTGG CTGACCAAGA CCAATGCATA AGGCATTATG AAGGCAGCAC    420

AGTCCCCGAA AAGAAGACAC CGAAGAGCCC TGTAGGGGTG CAGCCCATAC TGAATGAACA    480

CACCTTCTGT GCTGGCATGT CTAAGTACCA AGAAGACACC TGCTATGGCG ATGCGGGCAG    540

TGCCTTTGCC GTTCACGACC TGGAGGAGGA CACCTGGTAT GCGACTGGGA TCTTAAGCTT    600

TGATAAGAGC TGTGCTGTGG CTGAGTATGG TGTGTATGTG AAGGTGACTT CCATCCAGGA    660

CTGGGTTCAG AAGACCATAG CTGAGAACTA ATGCAAGGCT GGCCGGAAGC CCTTGCCTGA    720

AAGCAAGATT TCAACCTGGA AGAGGGCAAA GTGGACGGGA GTGGACAGGA GTGGATGCGA    780

TAAGATGTGG TTTGAACCTG ATGGGTGCCA GCCCTGCATT GCTGAGTCAA TCAATAAAGA    840

GCTTTCTTTT GACCC                                                     855
```

(2) INFORMATION FOR SEQ ID NO:2:

(i) SEQUENCE CHARACTERISTICS:
(A) LENGTH: 859 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:2:

```
GACGCCAAAG GCAGCTTTCC TTGGCAGGCC AAGATGATCT CCAGACATGG ACTCACCACT     60

GGGGCCACAC TGATCAGTGA CCAGTGGCTG CTGACCACTG CCCAAAACCT CTTCCTGAAT    120

CACAGTGAGA ATGCGACAGC CAAGGACATT GCCCCTACCT TAACACTCTA TGTGGGGAAA    180

AACCAGCTGG TGGAGATTGA GAAGGTAGTT CTCCACCCCG AGCGCTCTGT GGTGGATATC    240

GGGCTGATCA AGCTCAAACA GAAAGTGCTT GTCACTGAGA AAGTCATGCC TATCTGCCTG    300

CCTTCCAAAG ACTACGTAGC GCCAGGCCGC ATGGGCTATG TGTCCGGTTG GGGGCGGAAT    360

GTCAACTTTA GATTTACTGA ACGTCTCAAG TATGTCATGC TGCCTGTGGC TGACCAGGAG    420

AAGTGTGAGC TGCACTATGA GAAAAGCACA GTGCCTGAGA AGAAAGGCGC TGTAAGTCCT    480

GTTGGGGTAC AGCCCATCTT GAATAAGCAT ACCTTCTGTG CTGGCCTTAC CAAGTATGAG    540

GAAGACACTT GCTATGGTGA CGCTGGCAGT GCCTTTGCCG TCCATGACAC GGAGGAGGAC    600

ACCTGGTATG CAGCTGGGAT CCTGAGCTTT GACAAGAGTT GTGCCGTAGC TGAGTATGGT    660

GTGTACGTGA GGGCAACTGA TCTGAAGGAC TGGGTCCAGG AAACAATGGC CAAGAACTAG    720

TTCAGGGCTG ACTAGAGGGC TGCACACAGT GGGGCAGGGC AATTCACCCT GGAAGAGGAA    780

GTAGAAGGGT TGGGGACATA ATCTGAGGGC TGCTAGCCCT GCATTGCTCA GTCAATAATA    840

AAAAACGAGC TTTGGACCC                                                 859
```

(2) INFORMATION FOR SEQ ID NO:3:

(i) SEQUENCE CHARACTERISTICS:
(A) LENGTH: 19 amino acids
(B) TYPE: amino acid
(C) STRANDEDNESS: single
(D) TOPOLOGY: linear (ii) MOLECULE TYPE: peptide -continued (iii) HYPOTHETICAL: NO (iv) ANTI-SENSE: NO (v) FRAGMENT TYPE: N-terminal (xi) SEQUENCE DESCRIPTION: SEQ ID NO:3:

```
Ile Ile Gly Gly Ser Met Asp Ala Lys Gly Ser Phe Pro Cys Gln Ala
1               5                   10                  15

Thr Asn Cys
```

(2) INFORMATION FOR SEQ ID NO:4:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "primer"

(iii) HYPOTHETICAL: NO (iv) ANTI-SENSE: NO (xi) SEQUENCE DESCRIPTION: SEQ ID NO:4:

```
GACGCCAAAG GCAGCTTTCC TTGGCAGGCC                                      30
```

(2) INFORMATION FOR SEQ ID NO:5:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Forward primer"

(iii) HYPOTHETICAL: NO (iv) ANTI-SENSE: NO (xi) SEQUENCE DESCRIPTION: SEQ ID NO:5:

```
CCACCCATGG CAAATTCCAT GGCA                                            24
```

(2) INFORMATION FOR SEQ ID NO:6:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Reverse primer"

(iii) HYPOTHETICAL: NO (iv) ANTI-SENSE: NO (xi) SEQUENCE DESCRIPTION: SEQ ID NO:6:

```
GCTAAGCAGT TGGTGGTGCA GGA                                             23
```

(2) INFORMATION FOR SEQ ID NO:7:

(i) SEQUENCE CHARACTERISTICS:
(A) LENGTH: 20 base pairs

-continued (B) TYPE: nucleic acid
(C) STRANDEDNESS: single
(D) TOPOLOGY: linear (ii) MOLECULE TYPE: other nucleic acid
(A) DESCRIPTION: /desc = "Primer"

(iii) HYPOTHETICAL: NO (iv) ANTI-SENSE: NO (xi) SEQUENCE DESCRIPTION: SEQ ID NO:7:

CTCAAGTATG TCATGCTGCC 20

(2) INFORMATION FOR SEQ ID NO:8:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Primer"

(iii) HYPOTHETICAL: NO (iv) ANTI-SENSE: NO (xi) SEQUENCE DESCRIPTION: SEQ ID NO:8:

ACTACCTTCT CAATCTCCAC CAGC 24

(2) INFORMATION FOR SEQ ID NO:9:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Forward primer for human ENDO-I"

(iii) HYPOTHETICAL: NO (iv) ANTI-SENSE: NO (xi) SEQUENCE DESCRIPTION: SEQ ID NO:9:

GATGCCAAAG GCAGCTTTCC CTGGCAGGCT 30

(2) INFORMATION FOR SEQ ID NO:10:

(i) SEQUENCE CHARACTERISTICS:
(A) LENGTH: 28 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Reverse primer for human"

(iii) HYPOTHETICAL: NO (iv) ANTI-SENSE: NO (xi) SEQUENCE DESCRIPTION: SEQ ID NO:10:

CACACACAGG CCACGCGTCG ACTAGTAC 28

(2) INFORMATION FOR SEQ ID NO:11:

-continued

```
    (i) SEQUENCE CHARACTERISTICS:
         (A) LENGTH: 250 base pairs
         (B) TYPE: nucleic acid
         (C) STRANDEDNESS: double
         (D) TOPOLOGY: linear

   (ii) MOLECULE TYPE: other nucleic acid
         (A) DESCRIPTION: /desc = "Probefor human ENDO-I"

  (iii) HYPOTHETICAL: NO

   (iv) ANTI-SENSE: NO

   (xi) SEQUENCE DESCRIPTION: SEQ ID NO:11:

TTCCCACCAT AATCTCACCA CAGGTGCCAC GCTGATCAAT GAACAATGGC TGCTGACCAC      60

GGCTAAAAAT CTCTTCCTGA ACCATTCACA AAATGCAACA GCGAAAGACA TTGCCCCTAC     120

TTTAACACTC TATGTGGGGA AAAAGCACCT TGTAGAGATT GAAAAGGTTG TTCTACACCC     180

CAACTACTCC CAGGTAGATA TTGGGCTCAT CAAACTCAAA CAGAAGGTGT CTGTTAATGA     240

GAGAGTGATG                                                            250
```

ENDOMETRIOSIS-SPECIFIC SECRETORY PROTEIN

CROSS REFERENCE TO RELATED APPLICATIONS

This application is a Continuation-In-Part of U.S. Ser. No. 08/328,451, filed Oct. 25, 1994, now abandoned.

GOVERNMENT SUPPORT

The research carried out in connection with this invention was supported in part by a grant from the National Institute of Health, DHHS NICHD R29HD29026. The Government has certain rights in this invention.

BACKGROUND OF THE INVENTION

1. Field of the Invention

The present invention relates to the field of fertility and more particularly, to means and methods for determining and diagnosing endometriosis in women.

2. Description of Related Art

Endometriosis is defined as the ectopic presence of endometrial glands and stroma. Endometriotic tissue is comprised of tissue that is histologically similar yet biochemically and functionally different or out of phase from that of the uterine endometrium.

For example, endometriosis differs from its uterine counterpart in steroid responsiveness and receptor content [Vierikko, et al., 1985; Lessey et al., 1989; Melega et al., 1991] and expression of epidermal growth factor and epidermal growth factor receptor [Melega et al., 1991; Haining et a., 1991]. These altered characteristics, combined with an ectopic location, effect the physiological activity of the endometriotic tissue and thereby alter protein synthesis and secretion by the endometriotic tissue. Deviations in protein synthesis and secretion might be useful in developing unique markers for the nonsurgical diagnosis and management of endometriosis. Unfortunately, limited information is available concerning protein synthesis, secretion, regulation and expression in endometriotic tissue.

Applicant has found dissimilarities in protein synthesis and secretory patterns between eutopic and ectopic uterine tissues (endometriotic implants) using a rat model for endometriosis [Sharpe et al., 1991; Sharpe and Vernon, 1993]. Three endometriosis-associated proteins, synthesized and released in an alternate fashion from uterine proteins, were identified. Two endometriotic proteins named ENDO-I and ENDO-II by applicant ($M_r$ 40,000 to 55,000; pI 4.0 to 5.2 and $M_r$ 30,000 to 32,000; pI 7.0 to 9.0, respectively) were produced by endometriotic implants and not the uteri. The third protein ($M_r$ 70,000; pI 5.7), previously identified in uterine explant cultures as progesterone-induced uterine protein-1 (PUP-1) [Sharpe et al., 1991], appeared in endometriotic implant cultures 24–48 hours later than in uterine cultures [Sharpe and Vernon, 1993]. The identities, functions, mechanisms of altered protein synthesis and secretion by the ectopic uterine tissues and their correlation to the human endometriosis condition were not known at that time.

Little information in the literature addresses human endometriotic secretory proteins. Isaacson and coworkers [Isaacson et al., 1989] showed that human endometriotic tissues produce and secrete complement component 3 (C3) in an alternate fashion to that of the uterine endometrium. Secretion of C3 into the peritoneal cavity may elicit some of the immunological phenomena observed in patients with endometriosis and be related to the pathophysiology of the disease. However, while C3 may play a role in the pathophysiology of endometriosis, C3 is also produced by other tissues in the body and therefore is not useful in the development of an endometriosis-specific marker for the disease.

Further identification of biochemical dissimilarities between the uterine endometrium and endometriosis in vitro may enhance understanding of the mechanism(s) of the pathogenicity of the endometriotic tissue in vivo, potentially leading to the development of improved diagnosis and treatment for endometriosis. Therefore, Applicant desired to identify unique proteins synthesized and secreted by human endometriosis and endometrium in vitro and in vivo for the development of endometriosis-specific markers for diagnosis of the disease. Aberrant production or secretion of proteins by ectopic endometrium in the peritoneal cavity may contribute to the processes of endometriosis, infertility, pelvic adhesive disease and pelvic pain. A specific endometriosis-induced protein could be useful in diagnosis and nonsurgical management of the disease.

SUMMARY OF THE INVENTION

According to the present invention, a method of diagnosing endometriosis in a female patient suspected of having endometriosis is disclosed. The method includes the steps of obtaining a sample from the patient. The sample can be a fluid sample such as peritoneal fluid or serum. Alternatively tissue samples can be used in the method The sample is analyzed to detect the presence of ENDO-I glycoprotein or its mRNA in the sample compared to non-endometriosis controls who do not express ENDO-I. The protein is characterized by (i) a molecular weight of 40,000 to 55,000 as determined by two-dimensional SDS-PAGE polyacrylamide gel electrophoresis;

(ii) having an isoelectric point of 4.0 to 5.5; and (iii) being synthesized and secreted specifically by stromal cells of endometriotic tissue origin; and (iv) in humans having a cDNA as set forth in SEQ ID No:1.

The sample can be assayed for polypeptides/proteins by immunohistochemical and immunocytochemical staining, ELISA, RIA, immunoblots, Western blotting, immunoprecipitation, functional assays for angiogenesis and macrophage activation using established cell lines as is known in the art. In an alternative embodiment mRNA complementary to the nucleic acid sequence can be assayed by in situ hybridization, Northern blotting and reverse transcriptase-polymerase chain reaction (RT-PCR).

DESCRIPTION OF THE DRAWINGS

Other advantages of the present invention will be readily appreciated as the same becomes better understood by reference to the following detailed description when considered in connection with the accompanying drawings wherein:

(FIG. 3B) endometrial epithelial cell culture, day 12, cytokeratin mAb (<open arrow>, three-dimensional mound of epithelial cells; <arrowheads>, interconnecting tubular processes; ×200); (FIG. 3C) endometrial stromal cell culture, day 8, vimentin mAb (×400); (FIG. 3D) endometriotic epithelial cell culture, day 6, BMA 180/cytokeratin mAbs (×200); (FIG. 3E) endometriotic epithelial cell culture, day 8, cytokeratin mAb (×400); (FIG. 3F) endometriotic stromal cell culture, day 8, vimentin mAb (×400).

DETAILED DESCRIPTION OF THE INVENTION

Figure 1A:
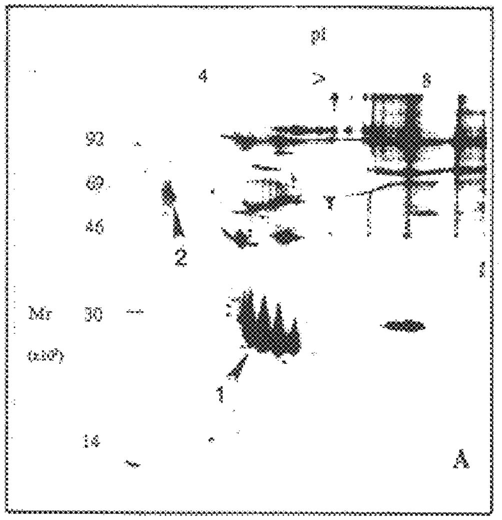
FIGS. 1A–D are representative two-dimensional SDS-PAGE fluoragraphs of L-[$^{35}$S] methionine-labeled secretory proteins from secretory phase endometrial epithelial cell (FIG. 1A), endometrial stromal cell (FIG. 1B), endometriotic epithelial cell (FIG. 1C), and endometriotic stromal cell (FIG. 1D) culture media.
Figure 1B:
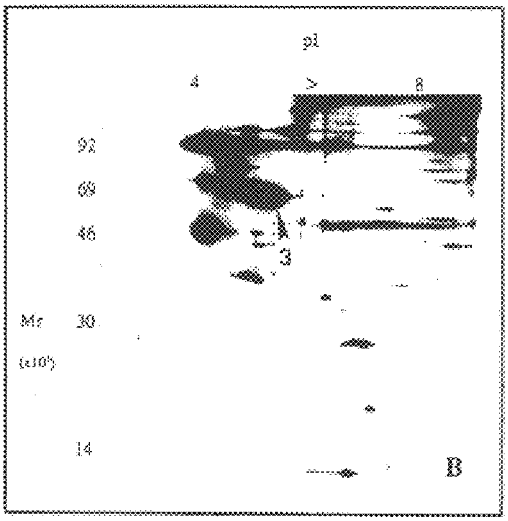

Generally, the present invention provides purified and isolated glycoprotein and biologically functional analogs thereof having specific physical and functional characteristics which characterize the invention over all known prior art for the diagnosis or endometriosis.

The glycoprotein is specifically an N-acetyl linked glycoprotein as determined by in vitro incorporation of D-[6-$^3$H]glucosamine and by binding to wheat germ agglutinin sepharose column (which "sees" certain N-acetylglucosamine and terminal sialic acid residues) [Sharpe et al., 1989, 1991, 1993].

A purified and isolated human glycoprotein named ENDO-I and analogues thereof are disclosed which has a molecular weight of 40,000 to 50,000 Da as determined by two-dimensional SDS-PAGE polyacrylamide gel electrophoresis and an isoelectric point of 4.0 to 5.5. (It should be noted that in some references ENDO-I is referred to as endometriosis protein group I to indicate the glycosylation variants.)

ENDO-I is a secretory protein which is synthesized and secreted by the endometriosis tissue (ectopic endometrial glands and stroma) but not uterine endometrium from women without endometriosis in vitro or in vivo. Reverse transcriptase polymerase chain reaction (RT-PCR) confirmed that ENDO-I transcripts are differentially expressed by endometriosis but not by uterine tissues from women without endometriosis. Human ENDO-I has a cDNA sequence as set forth in SEQ ID No:1.

Interestingly, human ENDO-I cDNA matches human haptoglobin B-chain with 5 mismatches indicating the ENDO-I may be a member of the haptoglobin superfamily. However, these mismatches provide significant changes in ENDO-I protein configuration folding or glycosylation [Dennis, 1995] providing changes in protein function [Pilotti et al, 1997] as well as unique epitopes for antibody recognition.

Rat ENDO-I has also been isolated and characterized. It has a molecular weight of 35,000 to 55,000 as determined by two-dimensional SDS-PAGE polyacrylamide gel electrophoresis and a cDNA sequence as set forth in SEQ ID No:2 as shown in Example 7. The N-terminal amino acid sequence of rat ENDO-I was also determined as described herein below and is set forth in SEQ ID No:3 (see Example 3).

The term Analogue as used herein is defined as a glycoprotein variant (alternatively the terms amino acid sequence alteration, amino acid sequence variant can be used) with some differences in their amino acid sequences as compared to the native human sequence encoded by the nucleic acid sequence of SEQ ID No:1 but with the same antigenic or biological function. Ordinarily the analogue will be generally at least 70% homologous over any portion that is functionally relevant. In more preferred embodiments the homology will be at least 80% and can approach 95% homology to the glycoprotein. The amino acid sequence of an analog may differ from that of the glycoprotein when at least one residue is deleted, inserted or substituted. Differences in glycosylation can provide analogs. The molecular weight of a glycoprotein can vary between the analog and the present invention due to carbohydrate differences.

Functionally relevant refers to the biological property of the molecule and in this context means an in vivo effector or antigenic function or activity that is directly or indirectly performed by a naturally occurring protein. Effector functions include but are not limited to include receptor binding, any enzymatic activity or enzyme modulatory activity, any carrier binding activity, any hormomal activity, any activity in promoting or inhibiting adhesion of cells to extracellular matrix or cell surface molecules, or any structural role. The antigenic functions essentially mean the possession of an epitope or antigenic site that is capable of cross-reating with antibodies raised against a naturally occurring endometriosis-associated protein ENDO-I. Biologically active ENDO-I analogues share an effector function of the native ENDO-I which may, but need not, in addition possess an antigenic function.

The purified and isolated glycoprotein of the present invention can be isolated by methods known in the art such as column chromatography. A specific example of a method is set forth in the Examples herein below. Further the protein of the present invention can be prepared recombinantly from the cDNA sequence as is known in the art.

The present invention further provides a method of diagnosing endometriosis in a female patient suspected of having endometriosis. The method includes the steps of obtaining a sample from the patient and analyzing the sample for the presence of ENDO-I (protein or mRNA) as compared to non-endometriotic controls who do not express ENDO-I.

In an embodiment a fluid sample can be obtained. The fluid sample can be peritoneal fluid or serum, saliva, tears, urine. In the preferred embodiment peritoneal fluid or serum is used. In a further embodiment a uterine tissue sample is used as shown in the Examples. Applicants have unexpectedly found that ENDO-I in addition to being synthesized and secreted specifically by stromal cells of endometriotic tissue origin in patients with endometriosis appears to be aberrantly expressed in the uterine tissue in patients with endometriosis. The uterine endometrial tissue sample can be obtained by standard methods known in the art.

The sample is analyzed to detect the presence of ENDO-I in the sample compared to non-endometriosis controls who do not have the protein present.

The sample is analyzed by methods known in the art. For fluid samples the method can include partial purification of the proteins from the sample by column chromatography. The tissue samples can be assayed for polypeptides/proteins by immunohistochemical and immunocytochemical staining (see generally Stites and Terr, *Basic and Clinical Immunology*, Appleton and Lange, 1994). The fluid samples can be analyzed by immunoassays such as ELISA, RIA, immunoblots, Western blotting, immunoprecipitation, functional assays for angiogenesis and macrophage activation using established cell lines as is known in the art. For endometrial tissue samples, the tissues/cells can be observed immunohistochemically for the presence of ENDO-I protein. Further, mRNA complementary to the target nucleic acid sequence can be assayed by in situ hybridization, Northern blotting and reverse transcriptase-polymerase chain reaction (RT-PCR). In a further embodiment, the tissue sample can be cultured and the culture media analyzed as with fluid samples (see also Examples).

Generally, a protocol can be used which includes the steps of obtaining either tissue/cell sample or a fluid sample from a patient. In some cases this will be done during a laparoscopic examination or D&C. Those skilled in the art will know the proper procedure for obtaining the sample. For example, peritoneal fluid is simply aspirated with a syringe from the peritoneal cavity. The date of the patients last menstrual period and use of any medication are also recorded. Endometriotic tissues and fluids are classified as proliferative (days 4 to 14) or secretory (days 15 to 28) according to the date of their last menstrual period. In the control studies to determine the method of the present invention (see Examples), endometrial dating and the presence of endometriosis was confirmed by histological evaluation of the endometrium. The present invention allows the diagnosis of endometriosis without surgical intervention.

As discussed herein, two-dimensional polyacrylamide gel electrophoresis, as exemplified in the example section below can be used for identification of the protein. Other methods, such as immunoblot analysis, ELISA radioimmunoassay may also be used.

For use in immunoassays, polyclonal and/or monoclonal antibodies may be prepared against ENDO-I. The immunogen may be a synthetic peptide based on the protein sequence data or prepared recombinantly by cloning techniques from the cDNA sequence or the natural gene product and/or portions thereof may be isolated and used as the immunogen. Such proteins or peptides can be used to produce antibodies by standard antibody production technology well known to those skilled in the art as described generally in Harlow and Lane, *Antibodies: A Laboratory Manual*, Cold Spring Harbor Laboratory, Cold Spring Harbor, N.Y., 1988. These antibodies may then be used to identify ENDO-1 and ENDO-2 by techniques well known to those skilled in the art including radioimmunoassay, ELISA or Western blot analysis [Joshi et al., 1981, 1982; Catty and Raykundalia, 1989; Hsu, 1981], immunocytochemically. Antibody fragments may also be prepared from the antibodies and include Fab, $F(ab')_2$, and Fv by methods known to those skilled in the art.

For producing polyclonal antibodies a host, such as a rabbit or goat, is immunized with the immunogen, generally with an adjuvant and, if necessary, coupled to a carrier; antibodies to the protein are collected from the sera. Further, the polyclonal antibody can be absorbed wuch that it is monospecific. That is, the sera can be absorbed against related immunogens so that no cross-reactive antibodies remain in the sera rendering it monospecific.

For producing monoclonal antibodies the technique involves hyperimmunization of an appropriate donor with the immunogen or immunogen fragment, generally a mouse, and isolation of splenic antibody producing cells. These cells are fused to a cell having immortality, such as a myeloma cell, to provide a fused cell hybrid which has immortality and secretes the required antibody. The cells are then cultured, in bulk, and the monoclonal antibodies harvested from the culture media for use.

For producing recombinant antibody (see generally Huston et al, 1991; Johnson and Bird, 1991; Mernaugh and Mernaugh, 1995), messenger RNAs from antibody producing B-lymphocytes of animals, or hybridoma are reverse-transcribed to obtain complimentary DNAs (cDNAs). Antibody cDNA, which can be full or partial length, is amplified and cloned into a phage or a plasmid. The cDNA can be a partial length of heavy and light chain cDNA, separated or connected by a linker. The antibody, or antibody fragment, is expressed using a suitable expression system to obtain recombinant antibody. Antibody cDNA can also be obtained by screening pertinent expression libraries.

The antibody or antibody fragment can be bound to a solid support substrate or conjugated with a detectable moiety or be both bound and conjugated as is well known in the art. (For a general discussion of conjugation of fluorescent or enzymatic moieties see Johnstone & Thorpe, *Immunochemistry in Practice*, Blackwell Scientific Publications, Oxford, 1982.) The binding of antibodies to a solid support substrate is also well known in the art. (see for a general discussion Harlow & Lane *Antibodies: A Laboratory Manual*, Cold Spring Harbor Laboratory Publications, New York, 1988 and Borrebaeck, *Antibody Engineering—A Practical Guide*, W. H. Freeman and Co., 1992) The detectable moieties contemplated with the present invention can include, but are not limited to, fluorescent, metallic, enzymatic and radioactive markers such as biotin, gold, ferritin, alkaline phosphatase, β-galactosidase, peroxidase, urease, fluorescein, rhodamine, tritium, $^{14}C$ and iodination.

The present invention further provides a kit for the practice of the method of the invention wherein an immunoassay is used in the identification of ENDO-I. The kit includes antibody directed against human ENDO-I and both positive (containing ENDO-I) and negative (non-endometriotic) control samples. The kit can also contain additionally the reagents to practice the detection means in the various immunoassays and other assays.

The present invention further provides a kit for the practice of the method of the invention wherein the mRNA for ENDO-I is used in the identification of the presence of ENDO-I. As shown in the examples the probe as set forth in SEQ ID No:11 is specific and is provided in the kit which further includes both positive and negative control samples. The kit may also contain additionally the reagents necessary for the methods associated with identification of the mRNA for ENDO-I.

As shown in the Examples there is a distinct difference in the synthesis and release of ENDO-I by human endometriosis and uterine endometrium in culture. Unique, endometriosis-specific secretory proteins are of importance in the development of novel diagnostic, prognostic and therapeutic methods for the management of endometriosis, thereby reducing the need for surgical intervention in the diagnosis and treatment of this disease. Furthermore, understanding biochemical dissimilarities between endometrium and endometriosis will enhance our knowledge of the etiology and/or pathophysiology of the endometriotic tissue potentially leading to new treatment approaches for the disease.

As shown in the Examples, ENDO-I ($M_r$ 40,000 to 55,000; pI 4.0 to 5.2) was synthesized and secreted by endometriotic cultures but not endometrial cultures from women with regular menstrual cycles, it can be the marker for endometriosis. In addition to its presence in all endometriosis explant culture and endometriosis stromal cell culture media from patients who were not receiving treatment for the disease, ENDO-I was also found in half of the endometriosis cultures derived from women who either had received danazol or had undergone a prior hysterectomy for endometriosis. The continued synthesis and secretion of ENDO-I by endometriotic tissues from women who had undergone these therapies may be one possible explanation for treatment failures. The distinct differences in endometriosis and endometrial protein synthesis and secretion observed add to the growing list of biochemical dissimilarities which exists between these two tissues.

The above discussion provides a factual basis for the use of ENDO-I for the diagnosis of endometriosis. The methods used with and the utility of the present invention can be shown by the following non-limiting examples and accompanying figures.

EXAMPLES

General Methods

General methods in molecular biology: Standard molecular biology techniques known in the art and not specifically described were generally followed as in Sambrook et al., *Molecular Cloning: A Laboratory Manual*, Cold Springs Harbor Laboratory, New York (1989), and in Ausubel et al., *Current Protocols in Molecular Biology*, John Wiley and Sons, Baltimore, Md. (1989) and in Perbal, *A Practical Guide to Molecular Cloning*, John Wiley & Sons, New York (1988), and in Watson et al., *Recombinant DNA,* Scientific American Books, New York. Polymerase chain reaction (PCR) was carried out generally as in *PCR Protocols: A Guide To Methods And Applications*, Academic Press, San Diego, Calif. (1990).

General methods in immunology: Standard methods in immunology known in the art and not specifically described were generally followed as in Stites et al. (eds), Basic and Clinical Immunology (8th Edition), Appleton & Lange, Norwalk, Conn. (1994) and Mishell and Shiigi (eds), Selected Methods in Cellular Immunology, W. H. Freeman and Co., New York (1980).

Immunoassays: Most of the techniques used in performing immunoassays are widely practiced in the art, and most practitioners are familiar with the standard resource materials which describe specific conditions and procedures. However, for convenience, the following paragraph may serve as a guideline.

In general, ELISAs are the preferred immunoassays employed to assess the amount of ENDO-I in a specimen. ELISA assays are well known to those skilled in the art. Both polyclonal and monoclonal antibodies can be used in the assays. Where appropriate other immunoassays, such as radioimmunoassays (RIA) can be used as are known to those in the art. Available immunoassays are extensively described in the patent and scientific literature. See, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521 as well as Sambrook et al, *Molecular Cloning: A Laboratory Manual*, Cold Springs Harbor, N.Y., 1989.

Specific, Methods

Endometriotic tissues, including red petechia and reddish-brown lesions, were obtained at the time of laparoscopic examination and confirmed by histological evaluation. Endometriotic tissues were classified as proliferative (days 4 to 14) or secretory (days 15 to 28) according to the date of the donor's last menstrual period. Use of medication was also recorded. Additional tissue specimens were transported to the laboratory in saline and dissected free of adnexa.

Endometriotic stromal cells were obtained by enzymatic dissociation and purified by a series of filtrations and sedimentations. Cells were enzymatically dissociated during a one hour incubation in Dulbecco's Modified Eagle's Medium/Ham's F-12 (DMEM/Ham's F-12) containing 0.5% collagenase, 0.02% deoxyribonuclease and 2% horse serum in a shaking incubator at 37° C. After one hour, the solutions containing the dissociated cells were filtered through an 88 $\mu$m nylon mesh filter. The stromal cell fractions that passed through the 88 $\mu$m filter were purified by gravity sedimentation and a final filtration through a 38 $\mu$m nylon mesh to remove epithelial cells. Cell viability (trypan blue exclusion) and number were evaluated.

Cell fractions were diluted to a density of $1\times10^6$ viable cells/mL and were plated in plastic organ culture dishes for a total of $8\times10^5$ viable cells in a surface area of 176.25 $mm^2$. Cultures were kept in a humidified incubator at 37° C. with 5% $CO_2$. Culture media consisted of DMEM/Ham's F-12 containing 10% heat-inactivated fetal bovine sera for the first six days of culture. By day 8 of culture, the cells had achieved approximately 95% confluence and protein studies were initiated. The media was replaced with serum-free minimal essential medium containing L-[$^{35}$S] methionine (20 $\mu$Ci/mL) for 24 hours. Incubations were terminated by centrifugation of the media at 3000×RPM for 15 minutes at 4° C. Media containing the de novo synthesized proteins were dialyzed ($M_r$ cut off 6–8000) against 1.0 mM tris, pH 8.2 at 4° C. and lyophilized.

As controls for the isolated stromal cell fractions, endometriotic tissue explants (approximately 100 mg wet weight) were incubated in MEM in the presence of L-[$^{35}$S] methionine (20 $\mu$gCi/mL). Within 30 minutes of collection, tissue explants were cultured for 24 hours at 37° C. on a rocking platform (6 cycles per minute) in a gaseous atmosphere of 50% nitrogen, 45% oxygen and 5% carbon dioxide. Tissue explant culture media were harvested and processed for protein analysis as described above for cell culture media.

Two-dimensional polyacrylamide gel electrophoresis (2-D SDS-PAGE) was used to evaluate the de novo synthesized radiolabeled endometriotic proteins. Aliquots of lyophilized cell culture and tissue explant media containing $1.5\times10^6$ non-dialyzable cpm (6,000 to 8,000 $M_r$ cutoff) were applied to the first dimension isoelectric focusing gels. Molecular weight markers were added to the polyacrylamide (12%) second dimension slab gels. Proteins separated by two dimensional SDS-PAGE were transferred to nitrocellulose membranes at one amp constant current for one hour and visualized by fluorography. The BioRad™ 2D Analyst software with BioRad Model 620 densitometer was used to create digital contour maps of images on the fluorographs made from the two-dimensional SDS-PAGE protein separations. Computer generated peak reports were used for qualitative comparison of proteins from the contour maps.

EXAMPLE 1

Isolation and Characterization of Glycoprotein

Materials and Methods

Endometrial and Endometriotic Tissue: Human tissues were obtained from randomly selected, informed volunteer patients routinely presenting to the physicians in the Department of Obstetrics and Gynecology at the University of Missouri Medical School as approved by the Institutional Review Board. Patients presented for a variety of routine diagnostic and therapeutic examinations including diagnosis of endometrial function, endometriosis, tubal ligation for sterilization, routine gynecological care and gamete intrafallopian transfer.

Endometrial tissue was obtained using a Pipelle™ (Unimar, Wilton, Conn.) endometrial suction curette. Endometriotic tissue was obtained at the time of laparoscopic examination. Peritoneal endometriotic implants, including red petechia and reddish-brown lesions, were elevated with biopsy forceps and the area circumscribed by either laser or sharp dissection. Powder-burn implants and cystic ovarian endometriosis were excluded from the study. Vernon and associates have shown [Vernon et al., 1986] that the metabolic activity of the reddish implants appears to be greatest when compared with the brown or black lesions. Ovarian endometriosis was excluded to eliminate the possibility of "contaminating" ovarian cells in the cell culture experiments. The date of the patients last menstrual period and use of any medication were also recorded. Endometrial and endometriotic tissues were classified as proliferative (days 4 to 14) or secretory (days 15 to 28) according to the date of their last menstrual period. Endometrial dating and the presence of endometriosis were confirmed by histological evaluation by the Pathology Department at the University of Missouri. Tissue specimens were transported to the laboratory in saline and, using a dissecting microscope, dissected free of adnexa. Epithelial and stromal cell cultures plus tissue explant cultures were processed as described below.

Epithelial and Stromal Cell Isolation And Purification: Epithelial and stromal cells were obtained by enzymatic dissociation and a series of filtrations and sedimentations according to the protocol of Osteen et al. [1989] with modifications described by Sharpe et al. [1992]. Briefly, cells were enzymatically dissociated from endometrial and endometriotic tissues during a 1 hour incubation in phenol-red free Dulbecco's Modified Eagle's Medium/Ham's F-12 (DMEM/Ham's F-12; Sigma Chemical Co., St. Louis, Mo.) containing 0.5% collagenase (Clostridium histolyticum, catalogue number 840–7018IH), 0.02% deoxyribonuclease (DNase, Sigma Chemical Co., St. Louis, Mo.) and 2% horse serum (Vector Laboratories, Burlingame, Calif.) in a shaking incubator at 37° C. After 1 hour, the solutions containing the dissociated cells were filtered through an 88 $\mu$m nylon mesh filter. The stromal cell fractions that passed through the 88 $\mu$m filter were further purified by gravity sedimentation and a final filtration through a 37 $\mu$m nylon mesh to remove remaining epithelial cells. Cell viability (0.04% trypan blue exclusion test) and number (Makler Counting Chamber, T.S. Scientific, Perkasie, Pa.) were evaluated in aliquots of the cells.

The epithelial cell fractions retained by the filters in the initial filtration step were subjected to a second enzymatic digestion for 30 to 45 minutes or until cell clumps were dispersed. The dispersed epithelial cell fractions were further purified by gravity sedimentation and selective attachment procedures [Sharpe et al., 1992]. Cell number and viability were evaluated as described for the stromal cell fractions.

Isolation and purification of epithelial and stromal cells yielded an average of $2.1\times10^4$ viable epithelial cells and $2.6\times10^5$ viable stromal cells per mg of tissue. Both stromal and epithelial cell fractions were diluted to a density of $1\times10^6$ viable cells/mL. Stromal cell suspensions (0.8 mL each) were plated in plastic organ culture dishes (Falcon 3037, Falcon Plastics, Oxnard, Calif.) for a total of $8\times10^5$ viable cells in a surface area of 176.25 $mm^2$. Epithelial cell suspensions (0.4 mL) were plated in Millicelle CM culture inserts (Millipore, Bedford, Mass.) coated with 0.2 mL of the extracellular matrix Matrigel® (non-diluted; Collaborative Research Inc., Bedford, Mass.) providing a total of $4\times10^5$ viable cells in a surface area of 78.50 $mm^2$. Aliquots of the epithelial cell suspensions were also plated on plastic cultureware for immunocytochemical analysis as Matrigel® often created an unacceptable background in the staining process. Other than the elimination of the high background staining, the results of the immunostaining did not vary between the two culture types (matrix vs plastic).

All cultures were kept in a humidified incubator at 37° C. with 5% $CO_2$. Culture media consisted of phenol-red free DMEM/Ham's F-12 containing 10% heat-inactivated fetal bovine sera (GIBCO/BRL, Grand Island, N.Y.) for the first 6 days of culture. By day 8 of culture, the cells had achieved approximately 95% confluence and protein studies were initiated. The cultures were rinsed 3 times with phosphate buffered saline and the media was replaced with serum-free minimal essential medium (MEM; Gibco/BRL, Grand Island, N.Y.) containing L-[$^{35}$S] methionine (20 $\mu$Ci/mL; Du Pont New England Nuclear, Boston, Mass.) for 24 hours. Incubations were terminated by centrifugation of the media at 3000×RPM for 15 minutes at 4° C. Media containing the de novo synthesized proteins were dialyzed ($M_r$ cut off 6–8000) against 1.0 mM tris (hydroxymethyl) aminomethane HCl, pH 8.2 at 4° C. and lyophilized.

Cell morphology was assessed and photomicrographed at plating (day 0) and days 4, 6, 8 and 12 at ×100, ×200 and ×400 magnification using a Nikon Diaphon™ inverted phase contrast microscope (Nikon, Inc., Garden City, N.Y.) with a Hoffman Modulation Contrast System (Modulation Optics, Inc. Greenvale, N.Y.). Cells were evaluated before and after immunostaining and with a hematoxylin counterstain.

A variety of intermediate filament protein, glycoprotein and secretory protein markers were used to assess the various cell types present in the endometrial and endometriotic cell cultures.

Studies were undertaken to identify a marker which would distinguish between endometriotic cells and peritoneal cells. Murine monoclonal antibodies (MAbs) against: cytokeratins 8, 18 and 19 (for epithelial cells; Biodesign clone NCL-5D3; Kennebunkport, Me.); vimentin (for stromal cells; Boehringer Mannheim clone V9; Indianapolis, Ind.); a human epithelial cell marker directed against a 200 kilo-Dalton glycoprotein, BMA 180 (also known as BW 495/36; for endometrial/endometriotic epithelial cells; Behringwerke AG, Marburg, Germany); and for pregnancy-associated endometrial $\alpha_2$ globulin ($\alpha_2$-PEG; C6H11; for secretory phase endometrial epithelial cells) were used to assess the cells at plating and on days 4, 6, 8 and 12. The $\alpha_2$-PEG (C6H11; 1:100) MAb was used as a marker of secretory phase epithelial cell purification and also as an indicator of physiological function in vitro by Western blot analysis of explant culture media separated by 2D-PAGE.

Single and double labeling immunocytochemical techniques were performed using the Vectastain® ABC (avidin:biotin complex peroxidase procedure) and ABC-AP (avidin:biotin complex alkaline phosphatase procedure) Kits (Vector Laboratories) as per manufacturer's instructions. Peroxidase activity was demonstrated by incubation with 3,3'-diaminobenzidine substrate yielding a brown intracellular precipitate which confirmed peroxidase staining. Alkaline phosphatase activity was demonstrated with the Vectastain® Alkaline Phosphatase Substrate Kit I-Vector Red yielding a pinkish-red stain which confirmed alkaline phosphatase activity. Cells were counterstained with hematoxylin. Cells incubated with phosphate buffered saline substituted in place of primary antibody were included as negative controls in all immunostaining procedures. Using inverted phase contrast microscopy, multiple fields (×200) per cell type were evaluated for the percent of reactive cells.

Tissue Explant Culture: As controls for the isolated epithelial and stromal cell fractions, endometrial and endometriotic tissue explants (approximately 100 mg wet weight) were incubated in MEM in the presence of L[$^{35}$S] methionine (20 $\mu$Ci/mL) as previously used by Sharpe et al. [Sharpe et al., 1991] and Sharpe and Vernon [Sharpe and Vernon, 1993]. Within 30 minutes of collection, tissue explants were cultured for 24 hours at 37° C. on a rocking platform (6 cycles per minute) in a gaseous atmosphere of 50% nitrogen, 45% oxygen and 5% carbon dioxide. Tissue explant culture media were harvested and processed for protein analysis as described above for cell culture media.

Two-Dimensional Electrophoresis and Western Blot Analysis: Two-dimensional polyacrylamide gel electrophoresis (2-D SDS-PAGE) was performed as previously employed by Sharpe et al. [1993] and Sharpe and Vernon [1993]. To evaluate the de novo synthesized radiolabeled proteins, aliquots of lyophilized cell culture and tissue explant media containing 1.5×10$^6$ non-dialyzable cpm (6,000 to 8,000 $M_r$ cutoff) were applied to the first dimension isoelectric focusing gels. Molecular weight markers (Pharmacia LKB Biotechnology, Inc. Piscataway, N.J.) were added to the polyacrylamide (12%) second dimension slab gels. Proteins separated by two dimensional SDS-PAGE were transferred to nitrocellulose membranes (Schleicher and Schuell, Keene, N.H.) at one amp constant current for one hour using the Hoeffer Transphor® Blot System (Hoeffer Scientific, San Francisco, Calif.) and visualized by fluorography. The BioRad 2D Analyst software with BioRad Model 620 densitometer was used to create digital contour maps of images on the fluorographs made from the two-dimensional SDS-PAGE protein separations. Computer generated peak reports were used for qualitative comparison of proteins from the contour maps. Due to the overload of protein in some of the two-dimensional SDS-PAGE gels and possible loss of resolution following transfer of the proteins to nitrocellulose prior to autoradiography, only protein groups representing at least 10% of the integrated intensity were evaluated. Quantitative comparisons between patients or between tissue/cell cultures were not made.

Results

Endometrial and Endometriotic Tissue Specimens: Twenty-nine specimens were evaluated (Table 1). Twenty-two of the specimens were obtained from women with histories of regular menses. Seven additional specimens were obtained from women with atypical or absent menstrual cycles. Specimens ranged from 29 mg to over 4 g in weight. Up to 100 mg of tissue was used for explant culture and remaining tissue was enzymatically dissociated for the cell culture experiments.

Protein Synthesis and Secretion: Patterns of proteins synthesis and secretion made from the isolated endometrial and endometriotic epithelial and stromal cell culture media from women with regular menses are shown in FIGS. 1A–1D. Of the hundreds of proteins visualized on the two-dimensional SDS-PAGE fluorographs, five major groups of unique proteins, unique to either endometrial or endometriotic cultures and each representing at least 10% or more of the total integrated intensity of the radioactivity, were resolved and identified.

Figure 1C:
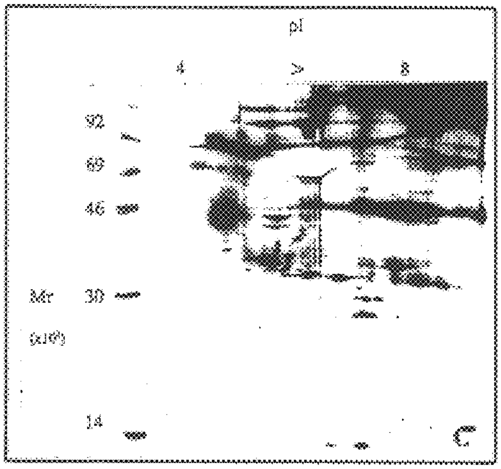
Figure 1D:
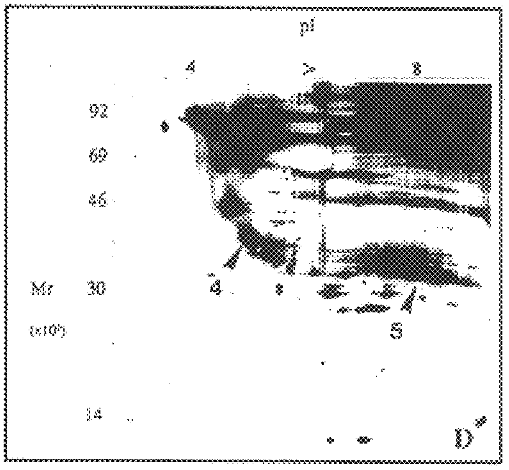

ENDOMETRIAL PROTEINS: Endometrial protein I ($M_r$ 25,000 to 27,000; pI 4.5 to 5.5) and endometrial protein II ($M_r$ 68,000 to 72,000; pI 3.0 to 3.2) were synthesized by secretory, but not proliferative phase, endometrial epithelial cells (FIG. 1A). Endometrial proteins I and II were not found in the culture media of endometrial stromal cells (FIG. 1B), endometriotic epithelial cells (FIG. 1C) or endometriotic stromal cells (FIG. 1D) regardless of the stage of the reproductive cycle. Endometrial protein III ($M_r$ 70,000; pI 5.7) was synthesized and secreted by secretory, but not proliferative phase, endometrial stromal cells. Endometrial protein III was also synthesized and secreted by two of seven proliferative endometriotic specimens (not shown) but none of the secretory phase endometriotic specimens tested (FIG. 1C and 1D). Thus, the proliferative phase release of endometrial protein III by endometriotic specimens was "out of phase" with that of the secretory phase uterine endometrial release of endometrial protein III.

ENDOMETRIOTIC PROTEINS: ENDO-I ($M_r$ 40,000 to 55,000; pI 4.0 to 5.2) and ENDO-II ($M_r$ 30,000 to 32,000; pI 7.0 to 9.0) were produced by endometriotic stromal cells (FIG. 1D) independent of menstrual cycle stage. ENDO-I and II were not synthesized by endometrial epithelial cells (FIG. 1A), endometrial stromal cells (FIG. 1B) or endometriotic epithelial cells (FIG. 1C) regardless of menstrual cycle stage.

Figure 2A:
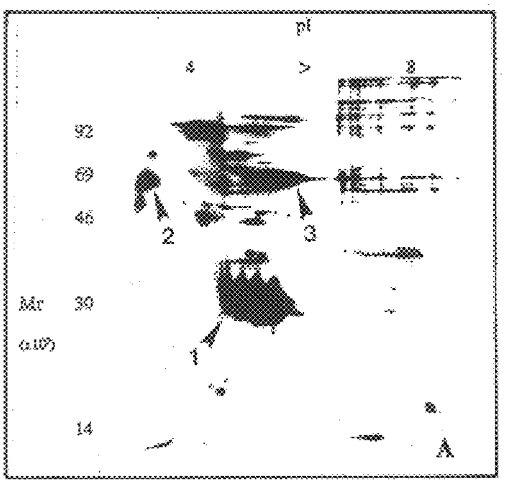
FIGS. 2A–B are representative two dimensional SDS-PAGE fluoragraphs of L-[$^{35}$S] methionine-labeled secretory proteins from secretory phase endometrial epithelial cell (FIG. 2A), and endometriotic (FIG. 2B) explant culture media.
Figure 2B:
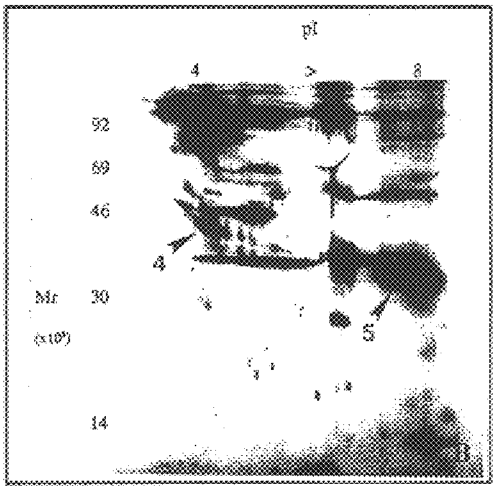

The pattern of ENDO-I synthesis and secretion visualized and evaluated in the cell culture media was identical to that evaluated in the explant culture media (FIG. 2A). Of interest is the finding that ENDO I was not found in endometriotic explant cultures from women with regular menses regardless of the phase of the menstrual cycle (FIG. 2B) while endometrial protein group III was synthesized and secreted by two of seven proliferative phase endometriotic specimens. Also paralleling the cell culture results, ENDO-I was found in endometriotic explant culture media (FIG. 2B) but not endometrial explant culture media (FIG. 2A) regardless of the menstrual cycle stage. Overall, no difference was noted in the pattern of endometrial protein synthesis and secretion between specimens from patients with and without endometriosis.

A limited number of specimens were cultured from women reporting atypical or absent menses. Proliferative endometrium from a patient with irregular uterine bleeding (no current medication) aberrantly synthesized and secreted secretory ENDO-I. This was the only case in which ENDO-I was produced by an endometrial biopsy specimen in this study. Subsequent histological diagnosis revealed adenomyosis also called endometriosis interna).

The pattern of protein synthesis and secretion was also evaluated from endometriotic tissue specimens obtained from patients taking danazol for endometriosis (n=2) and patients who had undergone a prior hysterectomy (n=2). Despite the fact that these women had received therapy for endometriosis, half (b=2/4) of these endometriotic specimens continued to synthesize and secrete ENDO-I.

Epithelial and Stromal Cell Culture

Figure 3A:
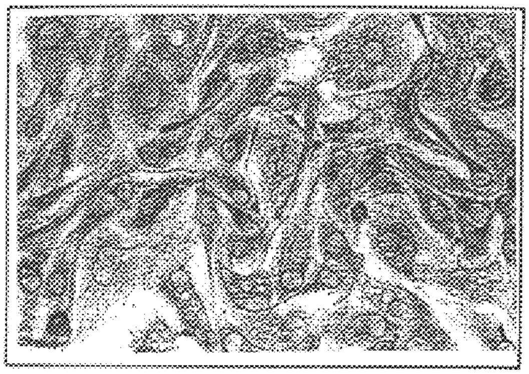
FIGS. 3A–F are photomicrographs of primary cultures of separated epithelial and stromal cells from endometrial and endometriotic biopsy specimens wherein (FIG. 3A) endometrial epithelial cell culture, day 8, cytokeratin mAb (×400)
Figure 3B:
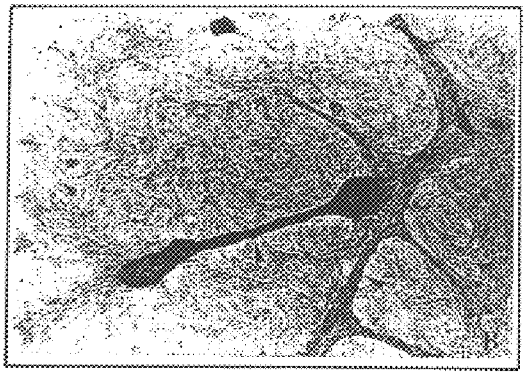
Figure 3C:
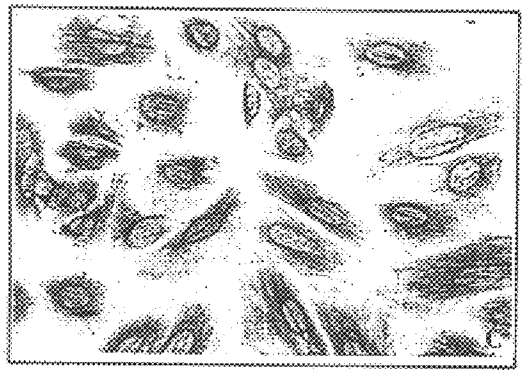

Morphologically, by day 8 of culture, endometrial epithelial cells cultured on the extracellular matrices plated on a semipermeable membrane appeared as homogeneous populations of tadpole-shaped cells with prominent, off-centered nuclei and whorling cell-cell processes that wrapped around adjacent cells (FIG. 3A). By day 12 of culture, the monolayers of endometrial epithelial cells formed three-dimensional mounds of cells which appeared interconnected by tubular processes resembling glandular-like structures (FIG. 3B). Endometrial stromal cells displayed a homologous, cobblestone mosaic-like, single cell monolayer pattern. The endometrial stromal cells had centrally located nuclei, distinct cytoplasmic borders which did not overlap and did not demonstrate cell-cell processes throughout the experiment (FIG. 3C).

Figure 3D:
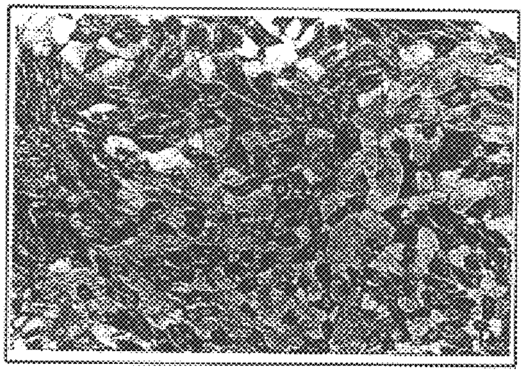
Figure 3E:
Figure 3F:
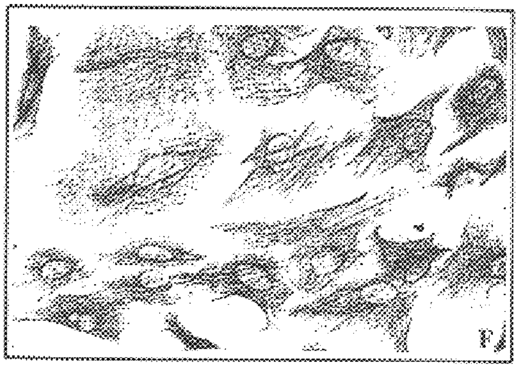

Cell fractions isolated from the endometriotic specimens contained morphologically and immunocytochemically distinct populations of cells. Subconfluent endometriotic epithelial cell fractions observed on days 4 and 6 (FIG. 3D) contained two layers of cells as determined by inverted phase contrast microscopy. An upper layer of cells with multiple long, ultrafine cell-cell processes appeared to be precursors to the tadpole-shaped endometriotic epithelial cells. A sublayer of larger, polymorphous-shaped cells displayed a continuum of cell morphology ranging from polygonal to elongated spindle-like shapes which were not observed in any of the endometrial epithelial cell cultures. By day 8 of culture (FIG. 3E), the surface layer had overgrown the sublayer so that the cells of the endometriotic epithelial cell cultures appeared tadpole-shaped and morphologically similar to the endometrial epithelial cell cultures (FIG. 3A). The endometriotic stromal cell fractions (FIG. 3F) appeared as single cell monolayers with cells which had centrally located nuclei, distinct cytoplasmic borders and no obvious cell-cell processes much like the morphology of the endometrial stromal cells (FIG. 3C).

The results of the immunocytochemical staining of the cells did not differ between the day of plating and days 4, 6, 8 and 12 and are presented in Table 2. Endometrial epithelial cells, especially those cells involved in formation of the epithelial cell mounds and tubular gland-like structures, displayed strong immunoreactivity with the cytokeratin and BMA 180 MAbs. Few (<3%) of the cells in the endometrial epithelial cells were decorated with the vimentin MAb suggesting limited stromal cell contamination of the epithelial cell cultures. Secretory, but not proliferative phase, endometrial epithelial cells were also decorated with the $\alpha_2$-PEG MAb (C6H11). The surface layer of tadpole-shaped endometriotic epithelial cells displayed similar immunostaining characteristics to the endometrial epithelial cells for cytokeratin, vimentin and BMA 180, but only the endometrial epithelial cells were decorated with the MAb raised against human $\alpha_2$-PEG (Table 2).

The surface and sublayers of the endometriotic epithelial cell cultures displayed different patterns of immunostaining (Table 2). While both layers stained positively for cytokeratin and negatively for $\alpha_2$-PEG, double antibody staining techniques revealed that only the upper layer of tadpole-shaped cells was decorated with the BMA 180 MAb (FIG. 3D) and only the polymorphous sublayer was decorated with vimentin.

Endometrial and endometriotic stromal cells were both decorated with the vimentin MAb and did not display immunoreactivity with the epithelial cell markers BMA 180 and $\alpha_2$-PEG. However, only the endometriotic stromal cells were decorated with the cytokeratin MAb.

EXAMPLE 2

The Synthesis and Release of Endometriotic Secretory Proteins Differs from that of the Uterine Endometrium To assess the ability of the endometriotic lesion to synthesize and secrete endometrial proteins, in vitro protein production by uterine endometrium and endometriotic tissues was examined. Matched biopsy specimens of uterine and endometriotic tissues were collected at the time of laparoscopic diagnosis for endometriosis. Menstrual cycle stage (n=5 follicular {cycle day 4–12} and 7 secretory {cycle day 19–27}) and the presence of endometriosis was documented histologically. Tissue explants plus isolated, purified, 90% confluent epithelial and stromal cells were cultured for 24 hours in minimal essential medium containing $^{25}$S-methionine (100 $\mu$Ci/ml). Tissue and cell culture media containing the de novo synthesized proteins was centrifuged, dialyzed and lyophilized and the proteins separated and visualized by two-dimensional gel electrophoresis and fluorography.

Although hundreds of similar proteins were produced by both tissue types, unique secretory products of the epithelial cells of the secretory uterine endometrium were found that were not secreted by the endometriotic tissue regardless of the cycle day. The two-dimensional electrophoretic mobility and distinctive epithelial cell secretory pattern suggest that one of these is $\beta$-lactoglobulin (pregnancy associated endometrial $\alpha$-globulin, $\alpha_2$-PEG), a major secretory protein of the glandular epithelium of the human endometrium. The second protein is not identified.

A protein was observed that was augmented in stromal cells of the uterine cultures as compared to the endometriotic cultures. This protein co-migrates with the rat progesterone-induced uterine protein-1 (PUP-1, also of stromal origin) and may be the human homologue for PUP-1.

Secretion of a further protein which was identified as ENDO-I (see Example 1) was enhanced in the stromal cells of the endometriotic cultures as compared to those of the uteri.

EXAMPLE 3

Applicants determined the partial amino acid sequence for the rat ENDO-I glycoprotein as set forth in SEQ ID No:3. Specifically, rat ENDO-I was given to the Protein Core Facility at the University of Missouri for amino acid sequencing. Partially purified, wheat germ lectin fractionated ENDO-I protein from stromal cell culture media were separated by 2D-PAGE and electrophoretically transferred to polyvinylidene difluoride (PVDF) membranes. A minimum of 50 pmol quantities of protein for amino acid sequencing "off blot" is required. Transfer to PVDF membranes overnight at 4° C. provided samples free of contaminants such as Tris, glycine, sodium dodecyl sulfate or acrylamide. Transferred proteins were visualized by Commassie blue staining and cut from the membrane for sequencing. $NH_2$-terminal sequence analysis was carried out by automated Edman degradation on an Applied Biosystems 470A gas phase sequencer with a Model 120A on-line phenylthiohydantoin analyzer.

The partial amino acid sequence for rat ENDO-I is as follows:

Ile Ile Gly Gly Ser Met Asp Ala Lys Gly Ser Phe Pro Cys Gln Ala Thr Asn Cys (SEQ ID No:3).

EXAMPLE 4

Human cDNA for ENDO-I in Endometrotic Tissue

As shown in the above Examples ENDO-I is synthesized and secreted by rat and human endometriotic explants and endometriotic stromal cells. Further, limited N-terminal sequence analysis (Example 3) showed that rat ENDO-I shares some sequence homology with haptoglobin (Hp).

In this Example the ENDO-I cDNA (see Example 7 for methodology of preparing cDNA) was cloned from human peritoneal endometriosis in order to determine the relative expression of the ENDO-I gene in different human tissues. All tissues were collected at the time of total abdominal hysterectomy. Messenger RNAs (mRNAs) were isolated using the microFast track kit (Invitrogen, CA) and reverse transcribed into the corresponding cDNAs. An adaptor primer (AP) that annealed to the polyA tail of all mRNAs was used so that the cDNAs reflected the total mRNA population in the different tissues.

The human RT-PCR primer and the probe for human ENDO-I Southern blot analysis are as follows:

RT-PCR

Forward primer for human ENDO-I
5'-GAT GCC AAA GGC AGC TTT CCC TGG CAG GCT-3' (SEQ ID No:9)
Reverse primer for human: Universal Amplification Primer from GIBCO-BRL
5'-CUA CUA CUA CUA GGC CAC GCG TCG ACT AGT AC-3' (SEQ ID No:10).

SOUTHERN BLOT

Applicants used a 250 bp DNA fragment that spans from nucleotide 39 to nucleotide 289 of human ENDO-I cDNA. Sequence of the probe (double stranded DNA)
5'-TTCCCACCATAATCTCACCACAGGTGCCACGCT GATCAATGAACAATGGCTGCT GACCACG-GCTAAAAATCTCTTCCTGAACCATTCA-CAAAATGCAACAGCGAAAGACAT TGCCCCTACTT-TAACACTCTATGTGGGGAAAAAGCACCTTGTAGA GATTGAAAAGGT TGTTCTACACCCCAACTACTC-CCAGGTAGATATTGGGCTCATCAAACT-CAAACAGAA GGTGTCTGTTAATGAGAGAGTGATG-3' (SEQ ID No:11).

To clone the ENDO-I cDNA, a polymerase amplification reaction (PCR) was performed using as the template the cDNA population of a human endometriosis sample, a gene specific primer (GSP) based on the Hp sequence and a universal amplification primer that annealed to the AP. To assess the relative expression of the ENDO-I gene in different human tissues, PCRs were carried out with two GSPs based on ENDO-I nucleotide sequence (see Example 7). GAPDH was used as the internal control.

Automated DNA sequence analysis of the peritoneal endometriosis cDNA identified 873 nucleotides that displayed 94.6% and 91% identity with human Hp and Hp-related (Hpr) proteins respectively. The four glycosylation sites at amino acids 23, 46, 50 and 80 of the Hp beta chain were conserved in ENDO-I. Densitometric analysis of ENDO-I gene expression revealed that peritoneal endometriosis produced 100 times more ENDO-I mRNA than endometrium from women without endometriosis. ENDO-I mRNA was undetectable in fallopian tube and in endometrium from women with fibroids.

EXAMPLE 5

Haptoglobin-related gene product has only been shown to be synthesized by fetal liver. It was therefore unexpected to find some sequence homology with rat ENDO-1 N-terminal amino acid sequence as indicated in Example 3.

Using Western Blot, culture media from a human endometriosis explant was examined. A polyclonal antibody raised against human ENDO-I recognizes a single band at approximately 55,000. A monoclonal antibody raised against human haptoglobin did not recognize this band. The anti-haptoglobin antibody stained a large band with a molecular weight less than 50,000. There was no cross-reactivity observed with these antibodies between the proteins. This demonstrates that human ENDO-I and haptoglobin are two distinct proteins.

This was also tested with rat ENDO-I.

Western Blot Analyses: Western blot analyses of 2D SDS-PAGE separations of rat endometriosis explant culture media as describe (12 $\mu$g total protein) were performed using rabbit anti-human Hp antibody (1:5000 dilution; DAKO, Carpenteria, Calif.) and mouse anti-human Hp antibody (1:2000 dilution; clone no. HG-36; Sigma Chemical Co., St. Louis, Mo.). Immunostaining was performed using biotinylated anti-rabbit or anti-mouse IgG as secondary antibodies and the Vectastain ABC kit for vinyl membranes as per manufacturer's instructions (Vector Laboratories, Burlingame, Calif.). Peroxidase activity was demonstrated by incubation with 3,3'-diaminobenzidine substrate yielding a brown pigment.

Western Blot Analysis

Western blot analysis using rabbit anti-human Hp antibody was sufficiently sensitive to demonstrate recognition of five to six of the isoforms of ENDO-I protein in 2D SDS-PAGE separations of rat endometriosis explant culture media. Mouse anti-human Hp antibody did not demonstrate immunoreactivity with rat ENDO-I. This demonstrates that rat ENDO-I is also similar but not identical to Hp.

Proteins sharing immunological epitopes with Hp have been reported including pregnancy-associated plasma protein A (PAPP-A), a glycoprotein that increases in concentration in serum through pregnancy [Bueller and Bersinger, 1989; Bischof and Meisser, 1989; Oh et al, 1992]. Further, proteins which share epitopes and antigenicity with Hp and Hpr have been used to diagnose and/or monitor prognosis and therapy in patients with diabetes, Alzheimer's disease and breast and prostate carcinoma among others [Johnson et al, 1992; Kuhadja et al., 1989; Kuhajda et al., 1994; Shurbaji et al., 1992; Dobryszycka, 1992]. Fortunately, Hp exhibits considerable polymorphism which permits distinct diagnosis between these diseases. For example, nine specific IIp $\alpha$1 and $\alpha$-2 variants have been detected in maternal sera of mothers carrying Down syndrome fetuses [Myrick, et al., 1990]. Genetic determination of Hp $\alpha$ subtypes and the calculation of their distribution and allele frequencies have become a significant and useful tool of forensic science for paternity testing and individualization. Assays have also been developed to differentiate between Hp and Hpr in human plasma to allow assessment of Hpr as a clinical marker of malignancy [Oh et al, 1992]. Thus, ENDO-I may represent a unique endometriosis-associated Hp-like protein that can assess the clinical status of endometriosis or as a nonsurgical diagnostic marker for the disease.

EXAMPLE 6

Interleukin-6 (IL-6) Up Regulates Expression of Endometriosis Protein-1 (ENDO-I) mRNA As discussed herein, rat and human endometriotic explants and endometriotic stromal cells synthesize and secrete a unique glycoprotein, ENDO-I. Rat and human ENDO-I partial cDNA sequences share significantly identity (>98%) with the $\beta$ subunit of rat and human haptoglobin (Hp) respectively. Furthermore, ENDO-I mRNA levels are 46-fold greater in pelvic endometriosis than in eutopic endometrium (P=0.024) as determined by semiquantitative RT-PCR, using GAPDH as the internal control. As IL-6 is thought to play an important role in the development of endometriosis and is known to stimulate transcription of haptoglobin mRNA in human liver, the present study was conducted to: (1) study the effects of human recombinant IL-6 on ENDO-I mRNA expression by endometrium from women with endometriosis (UE-E) and by matched samples of pelvic endometriosis (PE) and (2) assess the levels of endogenous IL-6 mRNA in UE-E and PE samples.

ENDO-I mRNA levels were determined by semiquantitative RT-PCR in UE-E and PE samples incubated with and without IL-6. IL-6 transcript levels were determined only in specimens incubated without IL-6. Explants of UE-E and PE were incubated with and without IL-6 (100 ng/ml) in minimal essential medium for 48 hours. Total RNA was isolated and reversed-transcribed into the corresponding cDNA's, using an adaptor primer (AP) that annealed to the poly A tail. Polymerase chain reactions (PCRs) were performed to assess the relative expression of ENDO-I, using a gene specific primer (GSP) based on the Hp sequence and a universal adaptor primer (UAP) that annealed to the AP sequence. Two GSPs were used to amplify the IL-6 fragment. GAPDH was the internal control. The PCR products were resolved in agarose gels and submitted to Southern blot analysis. The relative amount of ENDO-I and IL-6 transcripts were calculated by dividing the density of each ENDO-I or IL-6 band, respectively, by the density of its corresponding GAPDH fragment. Results between samples incubated with and without IL-6 were analyzed by t-test. Results: IL-6 increased the relative amount of ENDO-I transcript in 29-fold UE-E (P<0.001) and 2-fold in PE as compared to UE-E and PE cultured without IL-6, respectively. IL-6 relative transcript levels were 12-fold greater in PE than UE-E. Significant upregulation of endometrial ENDO-I expression by IL-6, combined with the increased level of IL-6 transcript in PE versus UE-E indicates ENDO-I expression in vivo by endometriosis is regulated by IL-6 of peritoneal origin.

EXAMPLE 7

Rat ENDO-I cDNA Isolation

Ribonucleic Acid (RNA) Isolation: For poly A-enriched RNA isolation, rat endometriotic implants, uteri and liver were excised from rats in the estrus and diestrus stages of their estrous cycle as determined by evaluation of vaginal cytology and appearance of the uteri at sacrifice. Tissues were both immediately frozen in liquid nitrogen upon removal from the body and collected following in vitro explant culture, lysed with guanidine isothiocyanate solution (In vitrogen; San Diego, Calif.) and frozen. Poly A-enriched messenger RNA was isolated from the different tissues using the In vitrogen Micro-FastTrack following manufacturer's instructions.

3' Rapid Amplification of cDNA Ends (RACE) and Reverse Transcriptase Polymerase Chain Reaction (RT-PCR): Complementary DNAs were amplified from rat tissues from three different experiments using the SuperScript II Reverse Transcriptase (GIBCO BRL, Gaithersburg, Md.) and the adapter primer from a 3' RACE kit (GIBCO BRL) following the procedure reported by Chenchik et al. [9]. ENDO-I cDNAs were amplified using the 3' RACE procedure in a final volume of 25 $\mu$l containing 0.5 $\mu$l of cDNA, 20 mM TRIS-HCl (pH 8.4 at 22 C), 50 mM KCl, 1.5 mM $MgCl_2$, 0.2 $\mu$M of each dATP, dCTP, dGTP and dTTP, 0.1 $\mu$M of universal amplification primer (UAP, GIBCO BRL), 0.1 $\mu$M of gene specific primer (GSP):

5'-GACGCCAAAGGCAGCTTTCCTTGGCAGGCC-3' (SEQ ID No:4)

corresponding to amino acids 7–16 of ENDO-I and the β-chain of rat Hp [10] and 1.25 U of Taq DNA polymerase (GIBCO BRL). For the 3' RACE of this cDNA a touchdown PCR program was used as follows: 1 min at 94° C. followed by 5 cycles of 94° C. for 30 sec and 72° C. for 5 min; then 5 cycles of 94° C. for 30 sec and 70° C. for 5 min; then 5 cycles of 94° C. and 68° C. for 5 min; followed by a 10-min final extension at 68° C. GAPDH cDNA amplification was performed using similar PCR reagent concentrations. In this case, two GSPs were used: a forward primer:

5'-CCACCCATGGCAAATTCCATGGCA-3' (SEQ ID No:5) corresponding to nucleotides 152–175 of GAPDH cDNA and a reverse primer:

5'-GCTAAGCAGTTGGTGGTGCAGGA-3' (SEQ ID No:6)

that anneals to nucleotides 451–473 of the GAPDH cDNA. Temperature parameters for this PCR were as follows: 25 cycles at 96° C. for 30 sec, 55° C. for 30 sec and 72° C. for 90 sec with 5 sec autoextension, followed by a 10 min final extension at 72° C.

The ENDO-I and GAPDH PCR products were examined, respectively, on 0.8 % and 1.2% agarose/ethidium bromide gels in 1×TBE buffer. A 1Kb Ladder (GIBCO BRL) was used as a DNA size marker.

Sequence Analysis of the 3' RACE Product: The 950-bp bands amplified from endometriosis and liver samples were electroeluted from agar [12]. First, the purified DNA fragments were sequenced with the fmol DNA Sequencing System (Promega, Madison, Wis.) following the supplier's recommendations. The ENDO-I GSP was end-labeled by polynucleotide kinase with $^{gama32}$P-CTP (3000 Ci/ml, New England Nuclear, Boston, Mass.) and used as the first sequencing primer. To obtain additional 3' sequence, another GSP:

5'-CTCAAGTATGTCATGCTGCC-3' (SEQ ID No:7)

that corresponded to ENDO-I nucleotide sequence 385–404 was designed. A third reverse GSP:

5'-ACTACCTTCTCAATCTCCACCAGC-3' (SEQ ID No:8)

that annealed to nucleotides at positions 186–209 of ENDO-I cDNA was designed to allow us to determine the sequence corresponding to the ENDO-I GSP region. In the last two cases, the sequencing reactions were performed by the University of Missouri DNA Core Facility using Applied Biosystems Prism Dye-Deoxy terminator FS chemistry and analyzed in the Applied Biosystems 377 automated DNA sequencer. The cDNA sequences were compared to known sequences in computerized databanks (Genetics Computer Group, Madison, Wis.).

The ENDO-I PCR fragment amplified from rat endometriosis was sequenced using three GSPs. The analysis shows that ENDO-I cDNA was almost identical to the β-chain of the rat Hp over the 859 bp overlap that corresponds to the coding sequence and the 3' untranslated region of the message. Only one nucleotide was different between ENDO-I and Hp cDNAs, nucleotide 476 of the ENDO-I PCR fragment was a G residue where as this corresponding nucleotide in rat Hp was a C.

Tissue Specific Gene Expression

Using the 3' RACE technique a 950 bp fragment was amplified from sets of rat endometriotic tissue cDNA and in rat liver cDNA (positive control) but not from rat uterus cDNA in three different experiments (see Example 7). This 950 bp fragment comprises coding sequence, 3' untranslated region, the poly A tail, the adapter primer and the universal amplification primer. As an internal control for mRNA/cDNA integrity, an RT-PCR of the housekeeping gene GAPDH was performed. The expected band of 320 base pairs was amplified from all three rat tissues. No difference in expression of the 950 bp transcript was observed between tissues frozen in liquid nitrogen upon excision from the rats or tissues lysed in guanidine isothiocyanate solution and frozen at −80° C. following in vitro explant culture.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains. The entire disclosure of the prior application, U.S. Ser. No. 08/328,451, filed Oct. 25, 1994, and assigned to the same assignee, is hereby incorporated in its entirety by reference into this application.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

TABLE 1

Source of Tissue Specimens

| Tissue Source | No. of specimens |
|---|---|
| Regular menses | |
| Matched endometrial/endometriosis biopsy | 16 |
| Endometrial biopsy only | 2 |
| Endometriosis biopsy only | 4 |
| Total | 22 |
| Atypical of absent menses | |
| Endometrial biopsy, irregular bleeding | 1 |
| Endometrial biopsy, irregular bleeding-MPA | 1 |
| Endometrial biopsy, perimenopausal | 1 |
| Endometriosis biopsy, danazol | 2 |
| Endometriosis biopsy, prior hysterectomy | 2 |
| Total | 7 |

TABLE 2

Immunocytochemical Staining of Isolated Populations of Endometrial and Endometriotic Epithelial and Stromal Cell Fractions

| | Epithelial cell fraction | | | Stromal cell fraction | |
|---|---|---|---|---|---|
| | Endometrial tissue Tadpole | Endometriotic tissue Tadpole | Endometriotic tissue Polymorph | Endometrial tissue Cobblestone | Endometriotic tissue Cobblestone |
| Cytokeratin | +* | + | + | o | + |
| Vimentin | o† | o | + | + | + |

TABLE 2-continued

Immunocytochemical Staining of Isolated Populations of Endometrial and Endometriotic Epithelial and Stromal Cell Fractions

| | Epithelial cell fraction | | | Stromal cell fraction | |
|---|---|---|---|---|---|
| | Endometrial tissue Tadpole | Endometriotic tissue Tadpole | Endometriotic tissue Polymorph | Endometrial tissue Cobblestone | Endometriotic tissue Cobblestone |
| BMA 180 | + | + | o | o | o |
| $\alpha_2$-PEG | s‡ | o | o | o | o |

*+, Immunoreactivity detected during proliferative and secretory phases of the menstrual cycle.
†o, no immunoreactivity detected in either phase of the menstrual cycle.
‡s, immunoreactivity detected only in secretory phase of the menstrual cycle.

References

Bischof and Meisser, 1989. Immunological heterogeneity of pregnancy-associated protein-A (PAPP-A). Effects on the radioimmunoassay of PAPP-A. Br J Obstet Gynaec 96:870–5.

Bueller and Bersinger, 1989. Antisera to pregnancy-associated plasma protein-A (PAPP-A) recognizes human haptoglobin. Br J Obstet Gynaec 96:867–9.

Catty and Raykundalia, 1989. ELISA and related enzyme immunoassays. In:Catty D (ed) Antibodies, a practical approach. IRL Press, Oxford. Vol II pp97–154.

Dennis, 1995. A review of the biological significance of carbohydrates on glycoproteins and methods for their analysis. Adv Exp Med Biol 376:1–11.

Dobryszycka, 1992. Relevance of haptoglobin in clinical medicine. Folia Histochemica et Cytobiologica 30:197–200.

Fodor et al, 1993. "Multiplexed biochemical assays with biological chips", *Nature* 364:555–556.

Haining et al. 1991. Epidermal growth factor in human endometrium: proliferative effects in culture and immunocytochemical localization in normal and endometriotic tissues. Hum Reprod 6:1200–5.

Hillam et al., 1974. Local antibody production against the murine toxin of *Yersinia pestis* in a golf ball-induced granuloma. Infect Immun 10:458–463.

Hsu et al. 1981. Use of avidin-biotin-peroxidase comples (ABC) in immunoperoxidase techniques: a comparison between ABC and unlabeled antibody (PAP) procedures. J Histochem Cytochem 29:577–580.

Huston et al, 1991. "Protein engineering of single-chain Fv analogs and fusion proteins" in Methods in Enzymology (JJ Langone, ed.; Academic Press, New York, NY) 203:46–88.

Isaacson et al., 1989. Production and secretion of complement component 3 by endometriotic tissue. J Clin Endocrin Metab 69:1003–9.

Johnson and Bird, 1991. "Construction of single-chain Fvb derivatives of monoclonal antibodies and their production in *Escherichia coli* in Methods in Enzymology (JJ Langone, ed.; Academic Press, New York, N.Y.) 203:88–99.

Johnson et al, 1992. Cerebrospinal fluid protein variations in common to Alzheimer's disease and schizophrenia. Applied and Theoretical Electrophoresis 3:46–53.

Joshi et al., 1981. Radioimmunoassay for a progestagen-associated protein of the human endometrium. J Clin Endo Metab 52:1185–1192.

Kawasaki E S. Amplification of RNA. In: PCR protocols: A Guide to Methods and Applications, Innis M A, Gelfand D H, Sninsky J J, White T J, eds. Academic Press, 1990, pp21–27.

Kuhadja et al., 1989. Haptoglobin-related protein (Hpr) epitopes in breast cancer as a predictor of recurrence of the disease. N Engl J Med 321:636–41.

Kuhajda et al., 1994. Fatty acid synthesis: a potential selective target for antineoplastic therapy. Proc Natl Acad Sci, USA 91:6379–83.

Knudsen, 1985. Proteins transferred to nitrocellulose as immunogens. Anal Biochem 147:285–288.

Lessey et al., 1989. Immunohistochemical analysis of estrogen and progesterone receptors in endometriosis: comparison with normal endometrium during the menstrual cycle and the effect of medical therapy. Fertil Steril 51:409–15.

Melega et al., 1991. Tissue factors influencing growth and maintenance of endometriosis. Ann NY Acad Sci. 622: 257–65.

Mernaugh and Mernaugh, 1995. "An overview of phage-displayed recombinant antibodies" in Molecular Methods In Plant Pathology (R P Singh and U S Singh, eds.; CRC Press Inc., Boca Raton, Fla.) pp. 359–365.

Myrick, et al., 1990. Identification of haptoglobin alpha-2FF variants in mid-trimester maternal serum as potential markers for Down syndrome. Applied and Theoretical Electrophoresis 1:233–41.

Oh et al, 1992. Quantitative differentiation of the haptoglobin-related gene product from haptoglobin in human plasma: a possible test of tumor-associated antigen. Hybridoma 11:1–12.

Osteen et al., 1989. Development of a method to isolate and culture highly purified populations of stromal and epithelial cells from human endometrial biopsy specimens. Fertil Steril 52:965–72.

Pilotti et al., 1997. Insular carcinoma: a distinct de novo entity among follicular carcinomas of the thyroid gland. Am J Surg Pathol 21(12):1466–73.

Sharpe, et al., 1991. Detection of a progesterone-induced secretory protein synthesized by the uteri but not the endometriotic implants of rats with induced endometriosis. Fertil Steril 55:403–10.

Sharpe et al., 1992. Proliferative and morphogenic changes induced by the coculture of rat uterine and peritoneal cells: a cell culture model for endometriosis. Fertil Steril 58:1220–9.

Sharpe and Vernon, 1993. Polypeptides synthesized and released by rat endometriotic tissue differ from those of the uterine endometrium in culture. Biol Reprod. 48:1334–1340.

Sharpe et al., 1993. Polypeptides synthesized and released by human endometriosis tissue differ from those of the uterine endometrium in cell and tissue explant culture. Fertil Steril 60:839–51.

Shurbaji et al., 1992. Expression of oncogenic antigen 519 (OA-519) in prostate cancer is a potential prognostic indicator. Am J Clin Path 1992; 97:686–91.

Vernon et al., 1986. Classification of endometriotic implants by morphologic appearance and capacity to synthesize prostaglandin F. Fertil Steril 45:801–806.

Vierikko et al., 1985. Steroidal regulation of endometriosis tissue: lack of induction of 17β-hydroxysteroid dehydrogenase activity by progesterone, medroxyprogesterone acetate, or danazol. Fertil Steril 1985; 43:218–224.

Weibel, 1979. Stereological Methods. In: Practical Methods for Biological Morphometry, Vol 1, New York: Academic Press pgs. 33–45.

What is claimed is:

1. A method of diagnosing endometriosis in a female patient suspected of having endometriosis by:

(a) obtaining a uterine endometrial tissue sample from the patient; and (b) detecting an aberrant expression of a protein in the sample, wherein the aberrant expression presence of the protein indicates a diagnosis of endometriosis, the protein designated ENDO-1 and characterized by (i) having a molecular weight of 40,000 to 55,000 as determined by two-dimensional SDS-PAGE polyacrylamide gel electrophoresis;

(ii) having an isoelectrlc point of 4.0 to 5.5;

(iii) being synthesized and secreted specifically by stromal cells of endometriotic tissue origin; and (v) being encoded in part by a cDNA sequence consisting of SEQ ID No: 1.

2. The method as set forth in claim 1 wherein the detecting step is reverse transcriptase-polymerase chain reaction of the tissue sample.

3. A kit to practice the method of claim 1 comprising a probe being encoded by a sequence consisting of SEQ ID No.: 11, and positive and negative control samples, and detection means for detecting the probe thereby indicating a presence of ENDO-I.

4. A purified, isolated nucleic acid encoding a portion of a protein designated ENDO-1 which is a marker for endometriosis wherein the nucleic acid is a cDNA sequence consisting of SEQ ID No: 1.

5. A method of diagnosing endometriosis in a female patient suspected of having endometriosis by detecting an altered expression of mRNA complementary to the nucleic acid sequence of claim 4 including the steps of:

isolating mRNA from a uterine endometrial tissue specimen from the patient; and assaying for mRNA complementary to SEQ ID NO: 1 and encoding ENDO-1 or an analog thereof with an assay selected from the group consisting of in situ hybridization, Northern blotting and reverse transcriptase-polymerase chain reaction, wherein increased expression of the mRNA complementary to SEQ ID NO: 1 as compared to expression in normal uterine endometrial tissue indicates a diagnosis of endometriosis in the patient.

* * * * *